(12) United States Patent
Kim et al.

(10) Patent No.: US 8,674,148 B2
(45) Date of Patent: *Mar. 18, 2014

(54) MANUFACTURING PROCESS FOR IODINATED AROMATIC COMPOUNDS

(75) Inventors: Han Seok Kim, Youngin-si (KR); Jong In Lee, Seoul (KR); Il Hoon Cha, Gwacheon-si (KR); Yoon Seo Lee, Yongin-si (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 103 days.

This patent is subject to a terminal disclaimer.

(21) Appl. No.: 13/295,965

(22) Filed: Nov. 14, 2011

(65) Prior Publication Data

US 2012/0059203 A1    Mar. 8, 2012

Related U.S. Application Data

(63) Continuation-in-part of application No. 12/663,625, filed as application No. PCT/KR2007/005227 on Oct. 23, 2007, now Pat. No. 8,084,654.

(51) Int. Cl.
*C07C 22/00* (2006.01)

(52) U.S. Cl.
USPC .......................................... 570/206

(58) Field of Classification Search
None
See application file for complete search history.

(56) References Cited

U.S. PATENT DOCUMENTS

| 4,746,758 A | 5/1988 | Rule et al. |
| 4,778,938 A | 10/1988 | Rule et al. |
| 4,786,713 A | 11/1988 | Rule et al. |
| 4,788,353 A | 11/1988 | Paparatto et al. |
| 4,810,826 A * | 3/1989 | Cook et al. ............ 570/203 |
| 4,861,929 A | 8/1989 | Miyake et al. |
| 4,895,992 A * | 1/1990 | Rule et al. ............ 570/203 |
| 8,084,654 B2 * | 12/2011 | Kim et al. ............ 570/183 |
| 8,309,775 B2 * | 11/2012 | Kim et al. ............ 570/206 |
| 2006/0161028 A1 | 7/2006 | Hidaka et al. |

FOREIGN PATENT DOCUMENTS

| EP | 0183579 A1 | 6/1986 |
| JP | 03-503412 | 9/1989 |
| JP | 7-330665 | 12/1995 |
| WO | 88/02358 A1 | 4/1988 |
| WO | WO 89/08631 | 9/1989 |
| WO | WO 89/08631 | 8/1991 |

OTHER PUBLICATIONS

A Search Report mailed Feb. 27, 2013, which issued during the prosecution of European Application No. 07833536, which corresponds to the present application.

Japanese Patent Application No. 2010-530907: Office Action dated Oct. 2, 2012, including reference cited therein with English translation attached.

* cited by examiner

*Primary Examiner* — Sudhakar Katakam
(74) *Attorney, Agent, or Firm* — McDermott Will & Emery LLP

(57) ABSTRACT

Disclosed is a method for preparing an iodinated aromatic compound. More specifically, disclosed is a method of preparing an iodinated aromatic compound by iodinating an aromatic compound in the presence of oxygen over a zeolite catalyst, in which the aromatic compound and a monoiodo analog of the aromatic compound, or a monoiodo aromatic compound, as raw materials, are allowed to react with iodine. In comparison with a method in which only the aromatic compound is used as a raw material without adding the monoiodo compound, the disclosed method can increase the productivity of diiodo compounds and the selectivity to a p-diiodo compound and, at the same time, suppress side reactions, thus lengthening the life span of the catalyst.

6 Claims, 4 Drawing Sheets

US 8,674,148 B2

MANUFACTURING PROCESS FOR IODINATED AROMATIC COMPOUNDS

CROSS REFERENCE TO PRIOR APPLICATIONS

This application is a Continuation-In-Part of U.S. application Ser. No. 12/663,625, filed Dec. 8, 2009 (now U.S. Pat. No. 8,084,654), which is the U.S. National Phase Application under 35 U.S.C. §371 of International Application No. PCT/KR2007/005227, filed Oct. 23, 2007. The contents of the above applications are hereby incorporated by reference.

TECHNICAL FIELD

The present invention relates to a method for preparing an iodinated aromatic compound, and more particularly to a method of preparing an iodinated aromatic compound by iodinating an aromatic compound in the presence of oxygen using a zeolite catalyst, in which the aromatic compound and its monoiodo compound, as raw materials, are allowed to react with iodine.

BACKGROUND ART

Technology of preparing halogenated aromatic compounds by aromatic compounds such as benzene or naphthalene to react with halogen (bromine, chlorine, iodine, etc) has been used in various commercial fields.

Typically, p-dichlorobenzene, which is prepared through the reaction of benzene with chlorine, is used as a raw material for preparing engineering plastic PPS (polyphenylene sulfide). Technology of preparing PPS by allowing p-dichlorobenzene to react with sodium sulfide in an N-methylpyrrolidone solvent is known as the Macallum process, and PPS is currently commercially produced through the Macallum process. However, because it is difficult to obtain a high-molecular-weight polymer only through the Macallum process, a curing process, as a post-process, is carried out to obtain the high-molecular-weight polymer, and PPS obtained through the curing process has a disadvantage in that it becomes brittle due to a crosslinking reaction or the like. Also, metal salts, such as sodium chloride (NaCl), are necessarily produced as reaction byproducts in the polymerization process, and cause serious problems in terms of the economic efficiency of commercial processes and the physical properties of the polymer.

As methods which can fundamentally eliminate the production of metal salts and enable linear polymers to be obtained, U.S. Pat. Nos. 4,746,758 and 4,786,713 and related patents suggest methods of melt-polymerizing p-diiodobenzene with sulfur.

Also, U.S. Pat. Nos. 4,778,938 and 4,746,758 disclose methods of preparing p-diiodobenzene by allowing benzene to react with iodine in the presence of oxygen over a zeolite catalyst. These patents disclose that a conversion rate to a diiodo compound is high, a selectivity to a p-diiodo compound, which is commercially useful, is high, and the oxidation of benzene or naphthalene as a raw material can be minimized.

However, in order to make this iodination technology commercially more useful, it is preferable to further increase the productivity of diiodo compounds and the selectivity to a p-diiodo compound. Also, said patents disclose that carbon deposits are produced due to the combustion of raw material and that the activity of the catalyst is reduced due to the carbon deposits. Furthermore, the carbon deposits thus produced or multi-iodinated high molecular impurities not only deactivate the catalyst, but also remain in the iodinated product, thus causing serious problems in a subsequent purification process.

SUMMARY OF INVENTION

The present inventors have conducted studies to solve the above-described problems occurring in the prior art and, as a result, found that, when an aromatic compound, such as benzene or biphenyl, and a monoiodo analog of the aromatic compound, or a monoiodo aromatic compound as raw materials, are allowed to react with iodine, the productivity of diiodo compounds and the selectivity to a p-diiodo compound can be increased, and the life span of a catalyst can be significantly increased, thereby completing the present invention.

Therefore, it is an object of the present invention to provide a method for preparing an iodinated aromatic compound, which can minimize the deactivation of a catalyst, increase the productivity of diiodo compounds from an aromatic compound and the selectivity to a p-diiodo compound and, at the same time, suppress side reactions.

To achieve the above object, the present invention provides a method of preparing an iodinated aromatic compound by gas phase iodination comprising iodinating an aromatic compound in the presence of oxygen over a zeolite catalyst, in which the aromatic compound selected from a mixture of an aromatic compound and a monoiodo analog of the aromatic compound, and a monoiodo aromatic compound is subject to react with iodine, and an amount of the oxygen is at least about one half the number of moles of iodine.

According to the present invention, an aromatic compound and its monoiodo compound, as raw materials, are subject to react with iodine, whereby the productivity of diiodo compounds and the selectivity to a p-diiodo compound can be increased and, at the same time, side reactions can be suppressed, thus lengthening the life span of a catalyst.

REFERENCE NUMERALS IN THE FIGURES

Figure 1:
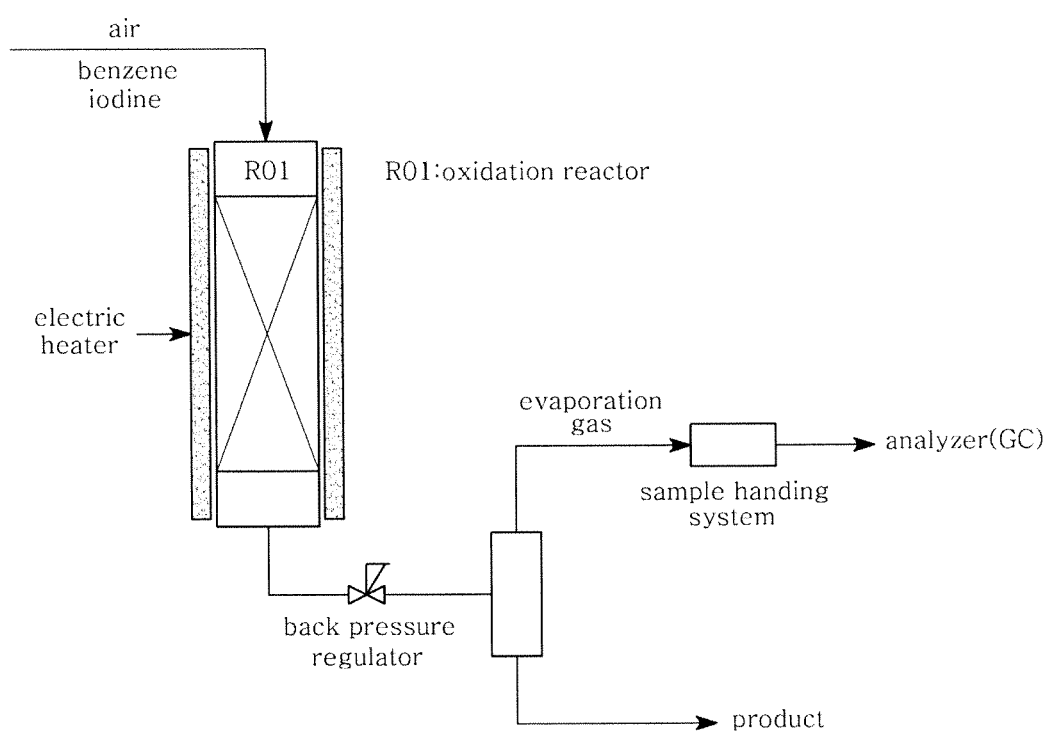
FIG. 1 is a schematic diagram showing a system and process for preparing an iodinated compound according to Comparative Example 1.

R01: an iodination reactor (packed with an Na-13X zeolite catalyst and equipped with an electric heater);
C10: distillation column 1 for removing water and benzene from a reaction product;
C20: distillation column 2 for separating and recycling monoiodobenzene and iodine from a reaction product;
C30: distillation column 3 for separating diiodobenzene through the top of the column and removing high-boiling-point substances, including triiodo compounds, through the bottom of the column;

back pressure regulator: serving to regulate reaction pressure and enabling a pressurized reaction to be carried out;

sample handling system: for removing vapor from gas in order to protect an analyzer in a post-process; and GC (gas chromatography): for measuring the content of carbon dioxide in gas.

BEST MODE OF INVENTION

Hereinafter, the present invention will be described in detail.

As described above, the present invention relates to a method for iodinating an aromatic compound in the presence of oxygen over a zeolite catalyst, wherein an aromatic compound and a monoiodo analog of the aromatic compound, or a monoiodo aromatic compound are used as raw materials, whereby the deactivation of the catalyst can be minimized, the productivity of diiodo compounds and the selectivity to a p-diiodo compound can be increased and, at the same time, side reactions can be suppressed, thus lengthening the life span of the catalyst.

According to the present invention, the iodination is carried out in a gas phase reaction, which is essentially free of liquid, thus all the feed materials are maintained as a gas phase during the reaction.

Also, in the present invention, it is possible to recycle the monoiodo compound and iodine by separating and purifying the reaction product, obtained according to the above method, through distillation.

In the present invention, as the catalyst for the iodination reaction, a Na-13X zeolite catalyst, which is commercially widely used, was used. In the present invention, various catalysts, including Y-type, ZSM5 and K-13X, were used to carry out the iodination of the aromatic compound, but the Na-13X catalyst was found to be most useful. It could be seen that the K-13X zeolite catalyst had low usefulness, such that the conversion of the aromatic compound and iodine was not greater than 50%, and the usefulness of the remaining catalysts was also lower than that of the Na-13X catalyst.

It is known that the iodination of aromatic compounds over a zeolite catalyst occurs over a wide temperature range of 200-400° C. In the present invention, the iodination reaction may be carried out under the temperature such that all the reactants are maintained in a gas phase. A temperature over about 400° C., however, is not preferred because at the temperature over about 400° C., unfavorable oxidation reactions of benzene may be activated which results in a loss of benzene by burning to CO, $CO_2$, and the like.

Meanwhile, the iodination reaction can be carried out at a wide range of reaction pressure up to about 10 bar and it could be seen that an increase in the reaction pressure up to about 10 bar led to an increase in the efficiency of the iodination reaction. According to one embodiment of the present invention, the iodination reaction is carried out under a pressure of lower than about 5 bar.

Meanwhile, hydroiodic acid (HI), which is produced during the iodination reaction, should be oxidized to iodine, which can participate in the reaction. For example, benzene or monoiodo benzene and iodine is reacted as shown in the following reaction equations:

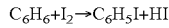

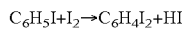

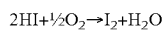

<Total Reaction>

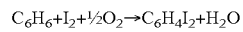

For this reason, the presence of oxygen in the reaction is considered to be essential. If oxygen is not present or the amount thereof is smaller than the amount of hydroiodic acid, hydroiodic acid will form azeotropes with water, generated during the reaction, and thus it will adversely affect a purification process after the reaction, and in addition, will severely corrode equipment due to its strong oxidation action. Accordingly, an amount of oxygen is an excess of the stoichiometric ratio of the oxygen to iodine, more specifically the amount of oxygen is not less than half the number of moles of iodine.

The molar ratio between the aromatic compound and iodine, which are used as raw materials, can vary. It can be seen that, as the amount of iodine was increased, the productivity of multi-iodinated aromatics was increased, but the conversion of iodine was decreased. However, if the ratio of the aromatic compound to the iodo compound is increased in order to increase the conversion of iodine, the conversion of iodine can be increased, but the productivity of the diiodo compounds will be reduced. For this reason, the ratio should be suitably adjusted according to the intended use of the reaction product.

Aromatic compounds, such as benzene or biphenyl, are converted to oxides, such as carbon dioxide, through an oxidation reaction, when they are in a condition of high temperatures in the presence of oxygen. This indicates the loss of raw materials. Herein, carbon dioxide is produced through complete oxidation, and can also form carbon deposits through incomplete oxidation or carbonization. The carbon deposits thus formed reduce the activity of the catalyst, thus shortening the life span of the catalyst.

According to the present invention, the productivity of diiodo compounds and the selectivity to a p-diiodo compound can be increased through the use of an aromatic compound and a monoiodo analog of the aromatic compound or a monoiodo aromatic compound as raw materials. Also, according to the method suggested in the present invention, the production of carbon dioxide and carbon deposits can be minimized, and thus the life span of the catalyst can be significantly lengthened, and high-quality iodinated compounds can be obtained.

According to the present invention, the aromatic compound is preferably one or more selected from benzene or biphenyl, and the monoiodo compound is preferably one or more selected from monoiodobenzene or monoiodobiphenyl, but the scope of the present invention is not limited thereto.

Figure 4:
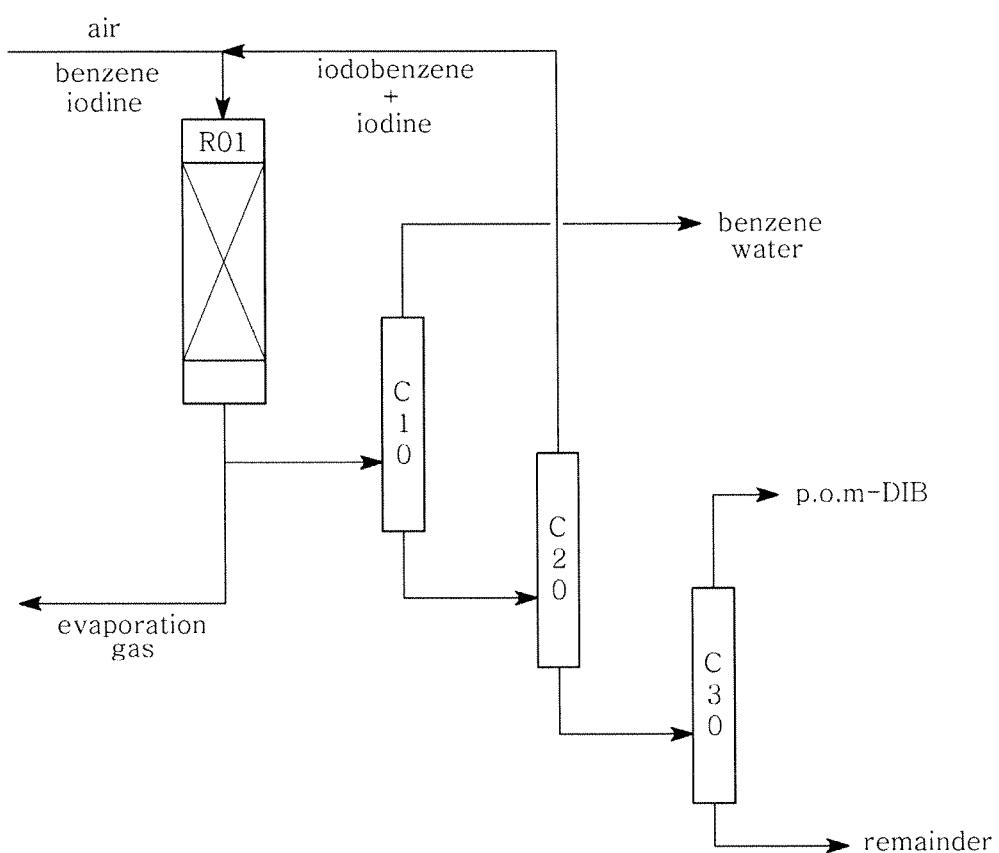
FIG. 4 is a schematic diagram showing a system and process for preparing an iodinated compound according to Example 4, in which the separation and recycling of a monoiodo compound and iodine are carried out.

Also, although the monoiodo compound can be prepared or purchased for use in the present invention, it is more efficient to separate and purify a monoiodo compound from the iodinated reaction product by distillation and recycle the separated compound, as shown in FIG. 4. Specifically, as shown in FIG. 4, the method of the present invention can be efficiently embodied by removing benzene and water in distillation column 1 (C10), separating monoiodobenzene and iodine through the top of distillation column 2 (C20), and introducing the separated materials into a reactor (R01).

In order to prove the effect of the present invention, the concept of the terms used in Comparative Examples and Examples, which are described later, will now be described. "Aromatic/iodine ratio" in reaction conditions indicates the molar ratio between the aromatic compound and the iodine that is used. When a diiodo compound is to be prepared, benzene should react with one mole of iodine (two iodine atoms). Thus, the aromatic/iodine ratio is defined by the following Math Figure 1:

Aromatic/iodine=(moles of benzene×2)+(moles of monoiodobenzene)/moles of iodine×2   Math Figure 1

The concept of the terms for examining a reaction product and the efficiency of a reaction process will now be described. The productivity of p-diiodobenzene (p-DIB) is defined as the production rate of p-diiodobenzene per unit volume of a catalyst per unit time, and is expressed in a unit of g/l·hr. The conversion of iodine and benzene is obtained by dividing the amount of iodine and benzene, converted to the reaction product, by the amount of iodine and benzene that is introduced, and then expressing the ratio as a percentage (%).

Figure 2:
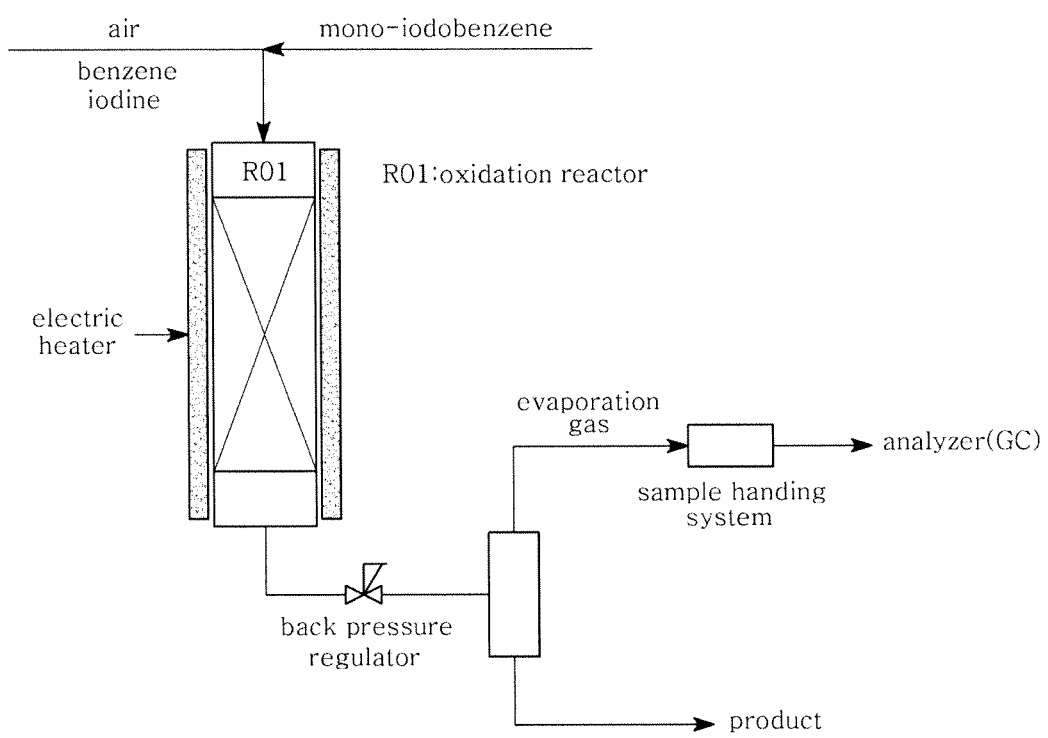
FIG. 2 is a schematic diagram showing a system and process for preparing an iodinated compound according to Examples 1 to 2.

Iodinated benzenes produced through the iodination reaction can be classified into the following compounds: mono-iodobenzene, obtained by reaction with one iodine atom; di-iodobenzene, obtained by reaction with two iodine atoms; and tri-iodobenzene, obtained by reaction with three iodine atoms. Among them, di-iodobenzene (DIB) and tri-iodobenzene (TIB) may each have three isomers. That is, for di-iodobenzenes, three isomers, including p-, o- and m-diiodobenzenes, are produced by the iodination reaction. Herein, total diiodobenzene (DIB) refers to the total of the weight percentages of p-, o- and m-diiodobenzenes contained in the reaction product, and is defined by the following Math Figure 2:

Total DIB=(p+m+oDIB)/(Product)×100   Math Figure 2

Figure 3:
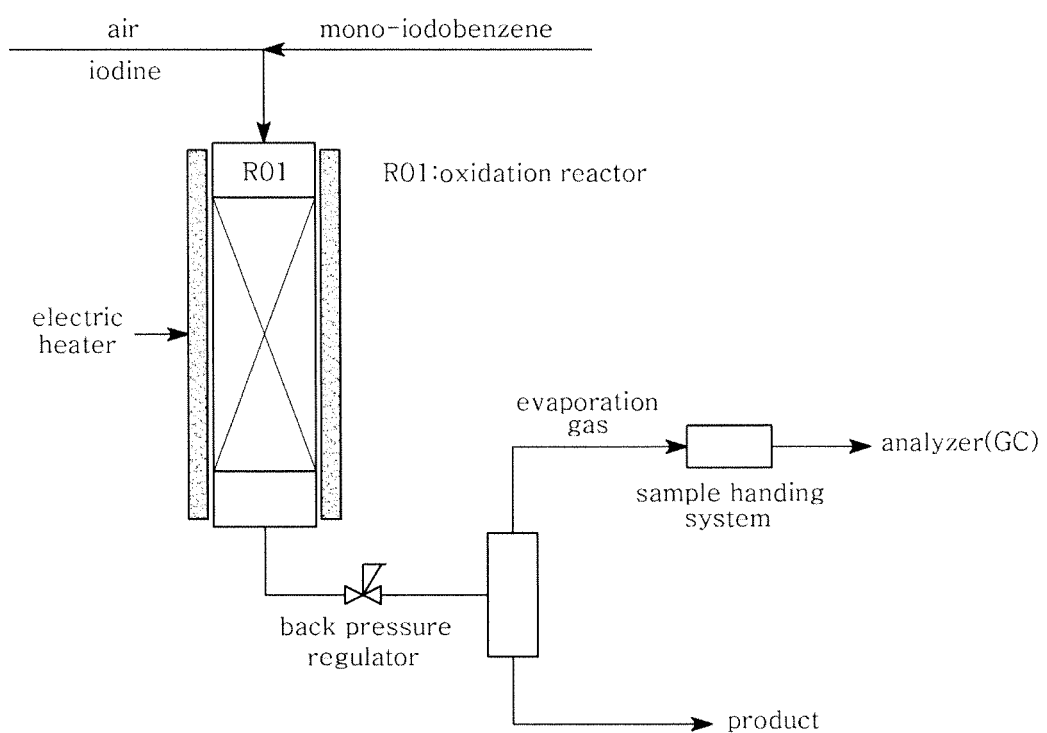
FIG. 3 is a schematic diagram showing a system and process for preparing an iodinated compound according to Example 3

Meanwhile, selectivity is expressed as a weight percentage of the concentration of the p-isomer among three diiodobenzenes contained in the reaction product, and is defined by the following Math Figure 3:

Selectivity=(p-DIB)/(p+m+oDIB)×100   Math Figure 3

According to the present invention, the p-diiodo compound, which is commercially highly valuable, can be prepared at high efficiency, and this high-efficiency preparation is made possible when the total DIB and the selectivity to the p-diiodo compound are high.

EXAMPLES

Hereinafter, the present invention will be described in further detail with reference to the following examples, but the scope of the present invention is not limited to these examples.

Comparative Example 1

In the system shown in FIG. 1, benzene (26.4 g/hr) and iodine (42.9 g/hr) were fed into a reactor without adding monoiodobenzene, and were subjected to a continuous iodination process under conditions of a reaction temperature of 280° C. and atmospheric pressure. 24 hours after the reaction conditions were reached, sampling and analysis were performed. The experimental conditions and results are shown in Table 1 below.

Example 1

In the system shown in FIG. 2, benzene (6.6 g/hr), monoiodobenzene (48.4 g/hr) and iodine (25.8 g/hr) were fed into a reactor and subjected to an iodination reaction under the same conditions as in Comparative Example 1. The experimental conditions and results are shown in Table 1 below.

Example 2

In the system shown in FIG. 2, benzene (16.5 g/hr), monoiodobenzene (38.5 g/hr) and iodine (38.8 g/hr) were fed into a reactor and subjected to an iodination reaction under the same conditions as in Comparative Example 1. The experimental conditions and results are shown in Table 1 below.

Example 3

In the system shown in FIG. 3, monoiodobenzene (55 g/hr) and iodine (17.1 g/hr) were fed into a reactor without adding benzene, and were subjected to an iodination reaction under the same conditions as in Comparative Example 1. The experimental conditions and results are shown in Table 1 below.

Example 4

In the system shown in FIG. 4, benzene (27.5 g/hr), monoiodobenzene (27.5 g/hr) and iodine (53.2 g/hr) were fed into a reactor and subjected to an iodination reaction in the same conditions as in Comparative Example 1. The experimental conditions and results are shown in Table 1 below.

TABLE 1

|  |  | Comparative Example 1 | Example 1 | Example 2 | Example 3 | Example 4 |
|---|---|---|---|---|---|---|
| Feed conditions |||||||
| Benzene | g/hr | 26.4 | 6.6 | 16.5 | 0 | 27.5 |
| Iodobenzene | g/hr | 0.0 | 48.4 | 38.5 | 55 | 27.5 |
| Iodine | g/hr | 42.9 | 25.8 | 38.8 | 17.1 | 53.2 |
|  | mol/hr | 0.169 | 0.1017 | 0.1529 | 0.0674 | 0.21 |
| Aromatic/iodine | Molar ratio | 2.0 | 2.0 | 2.0 | 2.0 | 2.0 |
| Air | ml/min | 220.0 | 100.0 | 200.0 | 80.0 | 200.0 |
| ($O_2$) | (mol/hr) | (0.1237) | (0.0562) | (0.1124) | (0.045) | (0.11245) |
| Composition of product |||||||
| Benzene | wt % | 9.84 | 3.63 | 7.71 | 0 | 9.78 |
| Iodobenzene | wt % | 44.31 | 38.53 | 44.01 | 45 | 44.25 |
| p-DIB | wt % | 22.99 | 40.47 | 33.96 | 38.97 | 30.78 |
| m-DIB | wt % | 9.21 | 6.76 | 6.21 | 7.84 | 6.88 |
| o-DIB | wt % | 2.92 | 1.88 | 1.98 | 2.12 | 2.54 |
| TIB | wt % | 3.11 | 5.19 | 3.49 | 5.65 | 3.24 |

TABLE 1-continued

|  |  | Comparative Example 1 | Example 1 | Example 2 | Example 3 | Example 4 |
|---|---|---|---|---|---|---|
| Characteristics | | | | | | |
| Productivity of p-DIB | g/l · hr | 69.97 | 123.17 | 103.36 | 118.60 | 93.68 |
| Conversion rate of $I_2$ | % | 91.38 | 88.41 | 90.20 | 92.44 | 90.50 |
| Conversion rate of benzene | % | 73.96 | 61.50 | 67.29 | — | 75.11 |
| Total DIB | wt % | 35.12 | 49.11 | 42.15 | 48.93 | 40.20 |
| Selectivity | % | 66.00 | 83.00 | 80.57 | 80.00 | 77.00 |
| $CO_2$ | % | 2.54 | 0.78 | 0.88 | 0.05 | 1.16 |

As can be seen in Table 1 above, Examples 1, 2, and 4, in which benzene and monoiodobenzene were fed and subjected to iodination, showed excellent results in terms of total DIB and the selectivity to diiodobenzene, compared to Comparative Example 1, in which only benzene was used as a raw material. Results similar thereto could also be observed in Example 3, in which monoiodobenzene was used as the raw material without adding benzene. The productivity of p-DIB was also high, when only monoiodobenzene was used as the raw material or when benzene was used together with monoiodobenzene. Thus, it could be seen that the production of the p-isomers per unit volume of the catalyst was efficiently achieved.

Comparative Example 2

An iodination reaction was carried out in the same manner as in Example 4 except that 0.0562 mol/hr of $O_2$ gas flow (i.e. 100.0 mL/min of air flow) was input with feed reactants to the reactor. As a result of analysis of the resulting product, the conversion rate of $I_2$ was 75.5%, which is lower than that of Example 4.

Comparative Example 3

An iodination reaction was carried out in the same manner as in Comparative Example 1, and the product was analyzed 200 hours and 400 hours after the initiation of the reaction.

Example 5

An iodination reaction was carried out in the same manner as in Example 4, and the product was analyzed 200 hours and 400 hours after the initiation of the reaction.

TABLE 2

|  | Conversion rate (%) of $I_2$ | | Black impurities (g) | |
|---|---|---|---|---|
|  | 200 hr | 400 hr | 200 hr | 400 hr |
| Comparative Example 3 | 80 | 65 | 1 | 3 |
| Example 5 | 87 | 82 | 0.13 | 0.38 |

As can be seen in Table 2 above, in the case of Comparative Example 3, the conversion of iodine was reduced to 80% after 200 hours and 65% after 400 hours, and the amount of black impurities detected in the product was increased with the passage of time. In the case of Example 5, the conversions of iodine after 200 hours and 400 hours were 87% and 82%, respectively, and the black impurities were detected in significantly small amounts, compared to those of Comparative Example 3. It is considered that the black impurities are carbon deposits contained in the products, and the carbon deposits reduce the activity of the catalyst. This can also be confirmed from the carbon dioxide productions of Comparative Example 1 and Examples 1 to 4, as shown in Table 1 above. In the case where benzene and monoiodobenzene are used, the concentration of carbon dioxide in gas was significantly reduced, compared to the case where only benzene was used as the raw material.

We claim:

1. A method of preparing p-diiodobenzene by gas phase iodination comprising the step of reacting (i) benzene and monoiodobenzene or (ii) monoiodobenzene as a starting aromatic raw material with iodine in the presence of oxygen and a zeolite catalyst at 200 to 400° C. to form p-diiodobenzene, wherein an amount of oxygen is not less than half the number of moles of iodine reacted.

2. The method of claim 1, wherein the gas phase iodination is essentially free of liquid.

3. The method of claim 1, wherein the gas phase iodination is carried out at a temperature such that all the feed materials are maintained in a gas phase.

4. The method of claim 1, wherein the gas phase iodination is carried out under a pressure of about 10 bar or less.

5. The method of claim 1, wherein the monoiodobenzene and the iodine are separated from the product of the gas phase iodination, and recycled to a reactor as raw materials.

6. The method of claim 1, wherein the starting aromatic raw material (i) contains at least 50% by weight of monoiodobenzene.

* * * * *